United States Patent [19]
Clark, Jr.

[11] Patent Number: 5,840,767
[45] Date of Patent: Nov. 24, 1998

[54] PERFLUOROCARBONS FOR BIOLOGICAL GAS EXCHANGE AND METHOD

[75] Inventor: Leland C. Clark, Jr., Cincinnatti, Ohio

[73] Assignee: Synthetic Blood International, Inc., Calif.

[21] Appl. No.: 565,782

[22] Filed: Dec. 1, 1995

[51] Int. Cl.$^6$ .................................................... A61K 31/02
[52] U.S. Cl. ......................................................... 514/759
[58] Field of Search ............................................. 514/759

[56] References Cited

U.S. PATENT DOCUMENTS

| | | |
|---|---|---|
| 3,911,138 | 10/1975 | Clark, Jr. . |
| 4,173,654 | 11/1979 | Scherer . |
| 5,158,536 | 10/1992 | Sekins et al. . |
| 5,295,953 | 3/1994 | Richard et al. . |
| 5,300,528 | 4/1994 | Graybill et al. . |
| 5,437,272 | 8/1995 | Fuhrman . |

FOREIGN PATENT DOCUMENTS

| | | |
|---|---|---|
| 9103267 | 9/1989 | WIPO . |
| 9219232 | 5/1992 | WIPO . |
| 9219300 | 12/1992 | WIPO . |

OTHER PUBLICATIONS

"Synthesis and Physical Properties of Perfluorocompounds Useful as Synthetic Blood Candidates", by R.E. More et al., Oxygen Carrying Colloidal Blood Substitutes, 1982, pp. 50–60.

Hoffman, R.E. et al., *Biomat., Art. Cells & Immob. Biotech.,* "Arterial Blood Gases and Brain Oxygen Availability Following Infusion of Intracheal Fluorocarbon Neat Liquids," 20(2–4), pp. 1073–1083, ©1992 by Marcel Dekker, Inc.

Leach, C.L. et al., *Critical Care Medicine*, "Perfluorocarbon–associated gas exchange (partial liquid ventilation) in respitory distress syndrome: A prospective, randomized, controlled study," vol. 21, no. 9, ©1993 by Williams & Wilkins.

Clark, L.C., Jr. et al. *Biomat., Art, Cells & Immob. Biotech.,* "Response of the Rabbit Lung as a Criterion of Safety for Flurocarbon Breathing and Blood Substitutes, " 20 (2–4), pp. 1085–1099, ©1992 by Marcel Dekker, Inc.

Tütüncü, A.S. et al., *American Review of Repiratory Disease,* "Comparison Ventilatory Support with Intracheal Perfluorcarbon Administration and Conventional...Acute Respiratory Failure,"vol. 148, pp. 785–792 (1993).

Samuel Schürch, John Georke, and John A. Clements, *Physiological Sciences*, "Direct determination of surface tension in the lung", vol. 73, No. 12, pp. 4698–4702, Dec. 1976.

Shaffer et al., *Biomaterials, Artificial Cells, and Immobilization Biotechnology,* "Artificial Cells, Blood Substitutes, and Immobilization Biotechology", vol. 22, No. 4, pp. 315–326 (1994).

*Primary Examiner*—Zohreh Fay
*Attorney, Agent, or Firm*—Klein & Szekeres, LLP

[57] ABSTRACT

Perfluorotetramethylcyclohexane shows improved properties for use in biological gas exchange, both as a blood substitute and as perfluorocarbon for intra-pulmonary applications. The material has an adequately low vapor pressure to completely avoid causing hyperinflated lung damage and to increase the interval between required applications. However, the compound has a sufficiently high vapor pressure to produce acceptably brief residence time within the body. A method has been developed for using this novel compound to accelerate the exhalation of very low vapor pressure compounds such as perfluorophenanthrene from the lungs. The addition of perfluorotetramethylcyclohexane, along with perfluorophenanthrene, greatly increases the rate at which the perfluorophenanthrene is exhaled.

22 Claims, 8 Drawing Sheets

PERFLUOROCARBONS FOR BIOLOGICAL GAS EXCHANGE AND METHOD

BACKGROUND OF THE INVENTION

1. Field of the Invention

The current invention concerns the field of therapeutic augmentation of oxygen exchange in mammals and, more specifically, improved perfluorocarbons and methods to use them in augmenting the breathing of a mammal having a lung disorder.

2. Description of Related Art

It has been known for some time that certain liquid perfluorocarbon chemicals (PFCs) can dissolve a significant volume of oxygen per volume of PFC. The present inventor was the first to show that these compounds could be used to support life in a mammal using liquid breathing, i.e., filling the lungs of the mammal with the perfluorocarbon liquid rather than with air or oxygen gas (see, L. C. Clark, Jr., F. Gollan. Survival of mammals breathing organic liquids equilibrated with oxygen at atmospheric pressure. Science 152:1755–56 (1966)).

By PFCs is meant those compounds in which virtually all of the hydrogens of a hydrocarbon are replaced by fluorine atoms. The term may also include similar compounds which also contain hetero-atoms such as nitrogen or oxygen so that the base compound, strictly speaking, is not a hydrocarbon. The important point is that these compounds have been shown to carry large quantities of oxygen and/or carbon dioxide and to show little or no toxicity to animals or humans.

The unusually favorable oxygen and carbon dioxide carrying properties of PFC liquids has also resulted in these compounds being used to create blood replacements (see, for example, U.S. Pat. No. Re. 33,451 to the present inventor). In fact, the use of PFCs as blood substitutes largely predates medical application of these compounds to therapies involving lung-based gas exchange. After early studies indicated that the perfluorocarbon chemicals were apparently inert and nontoxic, the task of selecting a PFC liquid for use as a blood substitute largely resolved into finding or synthesizing a compound with an ideal balance of vapor pressure and residence time.

Vapor pressure is extremely important because PFC liquids, such as some freons, which have relatively high vapor pressures can spontaneously form vapor bubbles in the blood stream. These bubbles can act as embolisms and are potentially life threatening. Generally, by selecting PFC liquids with boiling points well above normal body temperature (i.e., well above about 100° C.), the dangers of spontaneous PFC bubble formation can be largely avoided.

An important route whereby PFC therapeutics are lost from circulation or from the lung is by evaporation through the skin and/or lung. Thus, an additional advantage of using PFCs with higher boiling points is that evaporative loss is slowed thereby decreasing the amount of PFC that must be administered as a therapeutic and reducing the amount of PFC released to the environment. However, in the case of blood substitutes, by far the largest loss of PFCs from the circulation is through the reticuloendothelial system (RES), the body's blood filtration system which includes organs such as the spleen and the liver.

PFCs captured by the RES are, of course, not effective in transporting oxygen through the circulatory system. Furthermore, the residence time of PFCs in the organs of the RES can be as long as months or even years. Even though PFCs are believed to be generally nontoxic, there is concern over possible effect of long-term accumulation in the RES. To some extent this concern also affects intra-pulmonary uses of PFCs because of the possibility that extremely persistent PFCs might migrate from the lung to the RES, as well as the possibility that long-term PFC residence in the lungs is per se harmful. This residency problem sets up a tension in attempting to identify the ideal PFC for in vivo use. On one hand, although low vapor pressure compounds avoid the dangers of embolism, they may have excessively long residence time in the RES or the lungs. On the other hand, while higher vapor pressure compounds may tend to have shorter residence times in the RES or the lungs, they may also evaporate so rapidly as to significantly decrease the effective therapeutic lifetime of the PFC. Considerable research has been carried out to discover PFCs with an ideal balance of properties. See, for example, U.S. Pat. No. 3,911,138 to the present inventor incorporated herein by reference.

The very properties that make perfluorocarbon liquids useful in augmenting circulation-based gas exchange also make these compounds useful in augmenting lung-based gas exchange. In a number of different disease states abnormal mechanical characteristics of lung tissue inhibit gas-exchange. For example, if the surfactant normally produced in the lungs is absent or defective, the epithelial cells of the lung surfaces may adhere to one another, preventing the proper inflation of the alveoli, the tiny "air sacks" of the lung. Since the alveoli are primary sites of gas exchange, a deficiency of active lung surfactant normally results in significant respiratory distress. Also, certain diseases, such as emphysema, are characterized by damage to the lungs wherein scar tissue prevents normal lung inflation and effective gas exchange.

Following the pioneering PFC liquid breathing discoveries of the present inventor, methods of "tidal" liquid respiration were developed. These systems operate by pumping entire lungsfull of PFC liquid in and out of the lungs, with the goal that the PFC liquid would supply oxygen and also cause the inflation of alveoli even in the absence of lung surfactant. The complexity of equipment necessary to carry out tidal liquid respiration, combined with the patient risk should the equipment malfunction, have sharply limited application of this therapy. More recently, liquid respiration systems have been simplified by reducing the volume of PFC liquid to only the residual volume of the lungs, thereby allowing medical apparatus intended for ordinary gas-based assisted respiration to be employed. The residual volume of liquid appears to act somewhat like lung surfactant in ensuring inflation of the alveoli (see, for example, PCT patent application 92/19232 to Faithful et al. and U.S. Pat. No. 5,437,272 to Fuhrman).

The entire picture of obtaining an ideal PFC for medical applications was considerably complicated when the current inventor discovered that PFC liquids that had hitherto been considered absolutely harmless, such as perfluorodecalin (PFD), were actually capable of inducing a form of lung damage known as hyperinflated lung syndrome (HLS). Following the administration of certain PFC-based blood substitutes, the lungs of experimental animals appeared stiff and did not collapse normally when the chest wall was surgically opened.

HLS damage appears to be due to a plurality of bubbles trapped within or between the cells of the lung surface. Animals having severely affected lungs show considerable respiratory distress because their lungs have lost normal flexibility and cannot expand and contract in response to movements of the diaphragm. A possible theory of HLS etiology involves a situation where the vapor pressure of the PFC is sufficiently high that a significant amount of the chemical leaves a liquid droplet (i.e., a droplet in a blood substitute emulsion) and migrates through the aqueous phase of the blood. Finally, in passing from the aqueous phase of the blood into and through the cells of the lung, the perfluorocarbon molecules either invade a tiny preexisting gas bubble, or perhaps the local perfluorocarbon concentration becomes sufficient to allow a tiny bubble of perfluorocarbon vapor to form. At this point the bubble grows "osmotically" as dissolved atmospheric gases diffuse out of the liquid phase and into the bubble. This theory is explained in a article of which the present inventor is an author and which is incorporated herein by reference (see, "Response of the rabbit lung as a criterion of safety for fluorocarbon breathing and blood substitutes," Clark, L. C., Jr., R. E. Hoffman, and Stephanie Davis, In: *Biomaterials, Artificial Cells, & Immobilization Biotechnology*, 20(2–4):1085–99, Marcel Dekker, New York, 1992).

Initially, researchers believed that HLS was a danger only with intra-vascular use of PFCs. However, in investigating the HLS phenomena, the present inventor was dismayed to discover that those PFCs that cause HLS, when used intravascularly, can also cause HLS when instilled into the lungs as in various PFC liquid breathing therapies. That intratracheal PFC can also cause HLS suggests that the site of bubble formation within the lung tissue can be reached either from the vascular side or from the luminal side of the lung. Therefore, the many tests necessary for discovering an ideal PFC for either intravascular (blood) or intratracheal (lung) use must also include tests to rule out HLS production.

In summary, the ideal PFC for either blood or lung use would have a sufficiently high boiling point (i.e., low vapor pressure) to avoid either embolism or HLS. However, the ideal PFC would also have a sufficiently low boiling point (i.e., high vapor pressure) to prevent excessively long residence time within the animal or human body. Of PFCs having these acceptable properties, those with the slowest evaporation from the lungs are probably preferred for lung use to minimize the consumption of costly PFCs, the need to continually readminister PFCs to the patient, and the release of potentially environmentally harmful PFCs.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a safe perfluorocarbon liquid for intravascular use as a blood substitute and for intrapulmonary use as a surfactant substitute and as a gas exchange agent, as well as a novel method to remove persistent perfluorocarbon liquids from the lung.

It seems clear that the vapor pressure of any PFC liquid used for either artificial blood purposes or for intrapulmonary therapies is of extreme importance. However, PFC materials that are suitable for these purposes have very low vapor pressures (probably below 25 Torr) which are extremely difficult to measure with any accuracy. As a result, boiling points, which are considerably easier to accurately measure, are used in place of vapor pressure measurements. Boiling points of chemically homologous PFC liquids are approximately proportional to molecular weights, allowing boiling points to be estimated from the molecular weights with some accuracy. Table I shows a number of PFC liquids along with boiling point information.

TABLE I

| PFC | MW | BP[1] | HLS[3] |
|---|---|---|---|
| perfluorooctylbromide (PFOB) | 499 | 140.0 | yes |
| perfluorodecalin (PFD) | 462 | 139.0 | yes |
| perfluoromethyldecalin (PFMD) | 512 | 160.5 | no |
| perfluorophenanthrene (PFPA) | 624 | 215.0 | no |
| Isoamyl acetate[2] | 130 | 140.5 | — |

[1]Boiling Point measured in °C. at 750 Torr.
[2]Empirical standard with known boiling point of 142° C. at 760 Torr.
[3]HLS is pulmonary hyperinflation in the rabbit following IV injection.

From Table I. it is apparent that a PFC with a boiling point somewhere above about 141° C. is needed to avoid HLS. Both PFMD (160.5° C.) and PFPA (215° C.) have been shown not to cause HLS damage. However, both of these compounds have very long residence times in the lung and unacceptably long residence times in the RES when used in an emulsion as a blood substitute. Although long residence in the lung has not yet been associated with any damage, PFCs should probably not be allowed to remain indefinitely in the lung.

Figure 1:
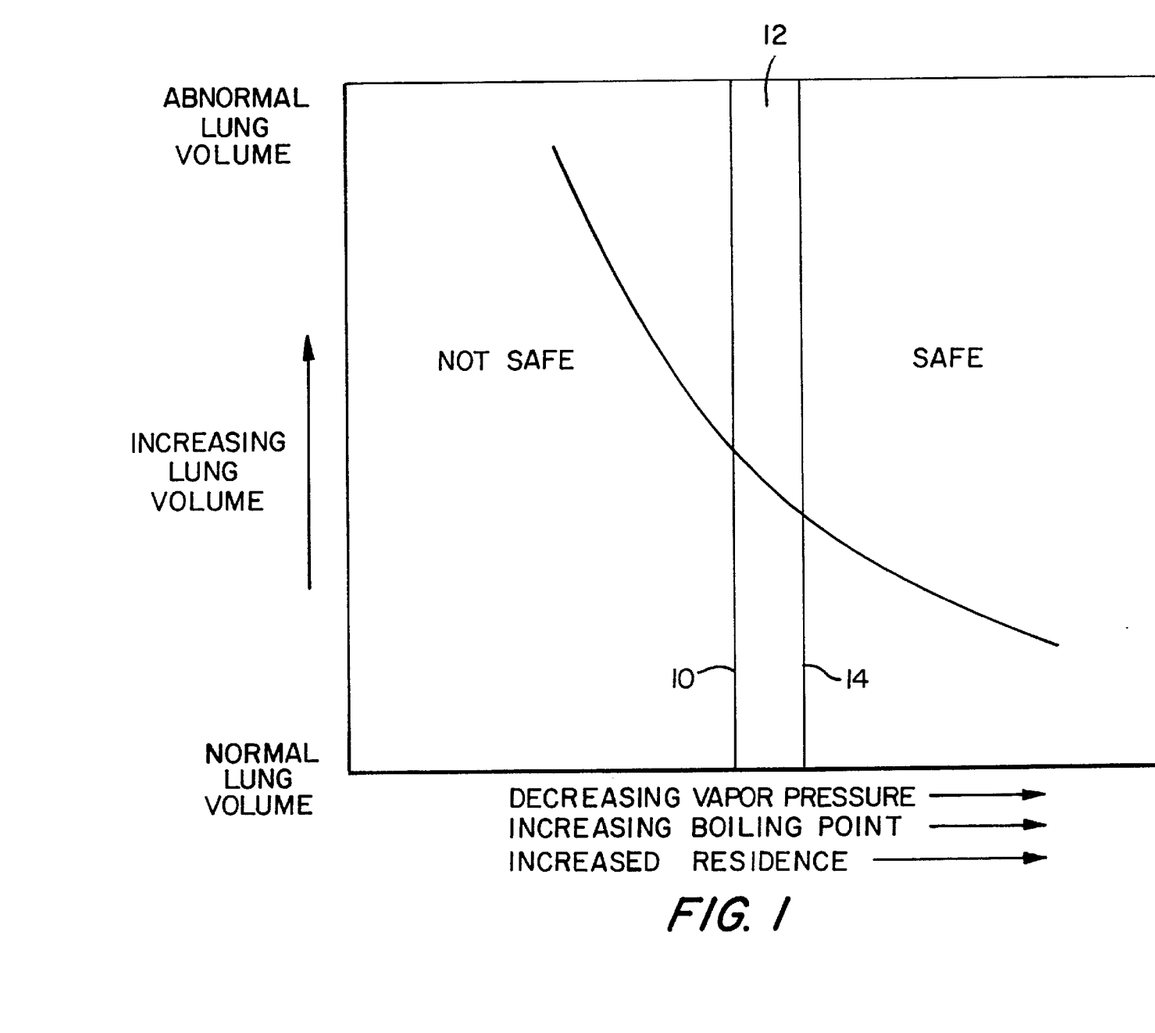
FIG. 1 shows a diagram displaying the characteristics used to estimate safety of perfluorocarbon liquids.

FIG. 1 shows a diagrammatic plot of lung damage versus boiling point and vapor pressure. A transition zone 12 is delimited by a first boundary 10 and a second boundary 14.

The first boundary 10 represents a boiling point of 141° C. because PFCs with boiling points much lower than this are known to cause HLS and, hence, are unsafe. Therefore, the ideal compound would fall somewhat above the first boundary 10. The second boundary 14 represents a boiling point of 160° C., the boiling point of PFMD, because compounds boiling at this point or higher are known to be safe. However, compounds with boiling points of 160° C. and higher are also known to have excessive residence times; therefore, the ideal compound would be below the second boundary 14.

The problem of excessive residence time with some high boiling point PFCs indicates that the desired compound should probably be as close to PFD or PFOB (acceptable residence times) as possible without causing any HLS damage. The molecular weight of the desired compound should lie somewhere between 462 (PFD) and 512 (PFMD). In addition, the compound should be readily synthesized with acceptably high purity.

Because both decalin and methyldecalin are cyclic, cyclic fluorinated compounds in the molecular weight range between these two compounds were tested. Perfluorotetramethylcyclohexane (PFTC, FLUOROVENT™, Synthetic Blood International, Inc., San Diego, Calif.) has unusually favorable properties. This compound has a molecular weight of 500 and a boiling point measured at 144.5° C. under the measurement conditions used for Table I.

PFTC can be synthesized from homologous hydrocarbons by alkylation using well-known techniques such as reaction with cobalt trifluoride in a furnace. There are a number of possible isomers of this material, depending on the structure of the starting material. Both 1,3,4,5 perfluorotetramethylcyclohexane and 1,2,4,5 perfluorotetramethylcyclohexane were tested and appear to have very similar or identical properties. The isomer most readily synthesized with high purity appears to be the 1,3,4,5 tetramethylcyclohexane isomer.

Figure 2:
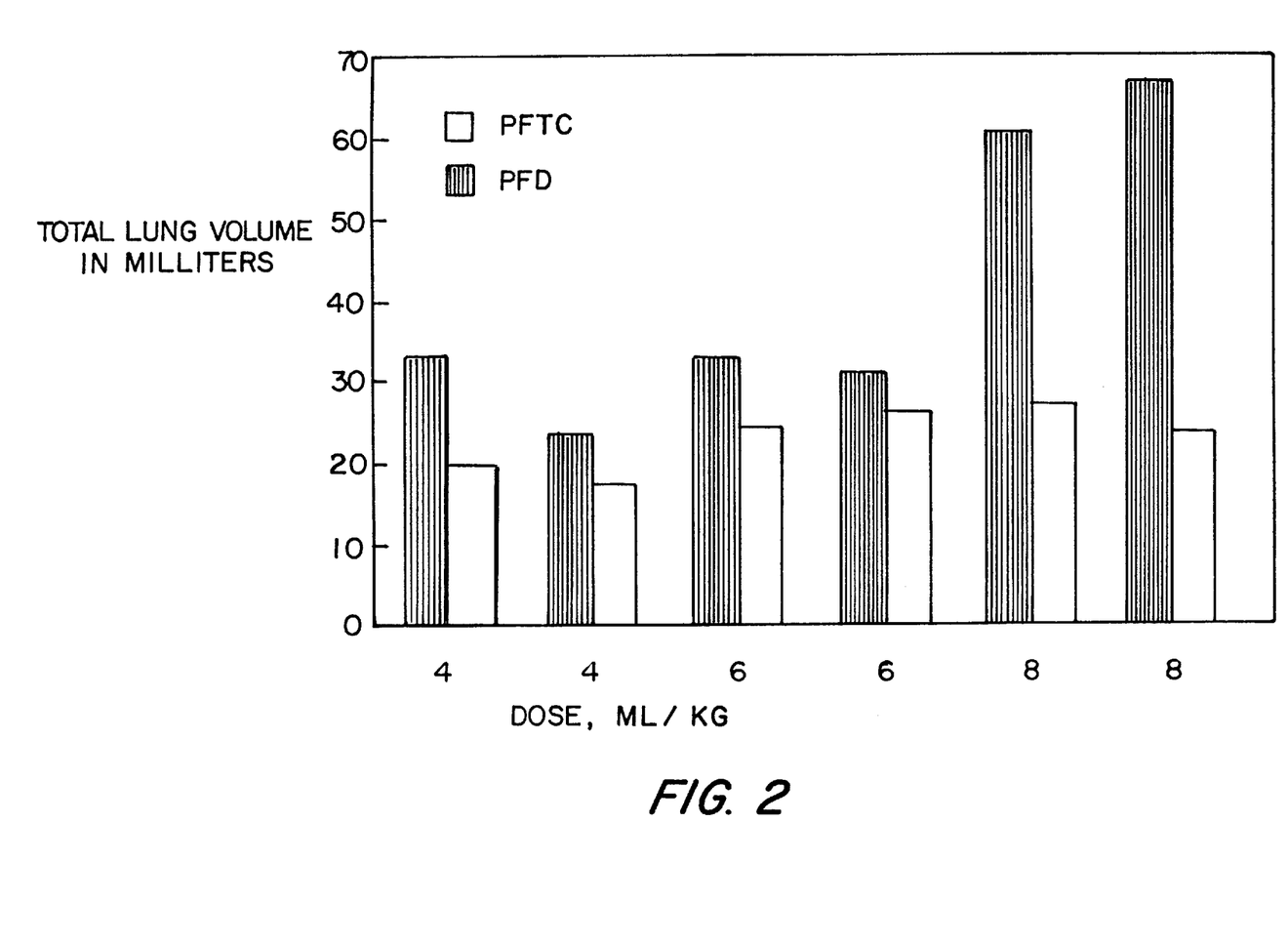
FIG. 2 shows a comparison of lung volumes in rabbits following the instillation of either perfluorodecalin or perfluorotetramethylcyclohexane.

FIG. 2 shows a comparison of results following PFD and PFTC instillation into the lungs of experimental rabbits. In this experiment high purity PFC liquids were instilled directly into the lungs of anesthetized animals by means of a catheter inserted through a tracheal slit. As shown on the horizontal axis, the animals received doses of between 4 and 8 ml/kg of body weight. These doses are at least as great as those used in most liquid PFC breathing protocols. Following instillation of PFC the animals rapidly recovered from the procedure and appeared normal.

Four days later the animals were sacrificed and the volumes of their lungs were measured (vertical axis). Lungs of the PFD treated animals all show a significantly greater volume than those of the PFTC treated animals. This increased volume is due to HLS, which prevents the lungs from collapsing normally. The PFTC lungs show a slightly greater volume than normal lungs, but this effect is due to a residual volume of PFTC remaining in the lungs distending them.

These results indicate that the boiling point of PFTC is sufficiently high (vapor pressure sufficiently low) to avoid HLS. However, the vapor pressure also appears to be high enough to avoid excessive residence time in the lungs or tissues (if used in a blood substitute). One way to judge the residence time is to measure the rate of transpiration (skin and lungs) or exhalation (lungs) for different PFCs.

To determine intrapulmonary residence time young laboratory rats (200–300 g body weight) were intratracheally dosed at 6 ml/kg with PFCs. Following administration of PFC, each animal was placed in a special sealed chamber through which was flowed fresh air at a controlled volume of one liter per minute. The air exiting the chamber was monitored for PFCs using an electron capture detector connected to a gas chromatograph. The system was calibrated with known amounts of PFCs, thereby allowing the identification of individual PFCs in mixtures, as well as calculation of the rates of PFC loss in microliters per day.

Figure 3:
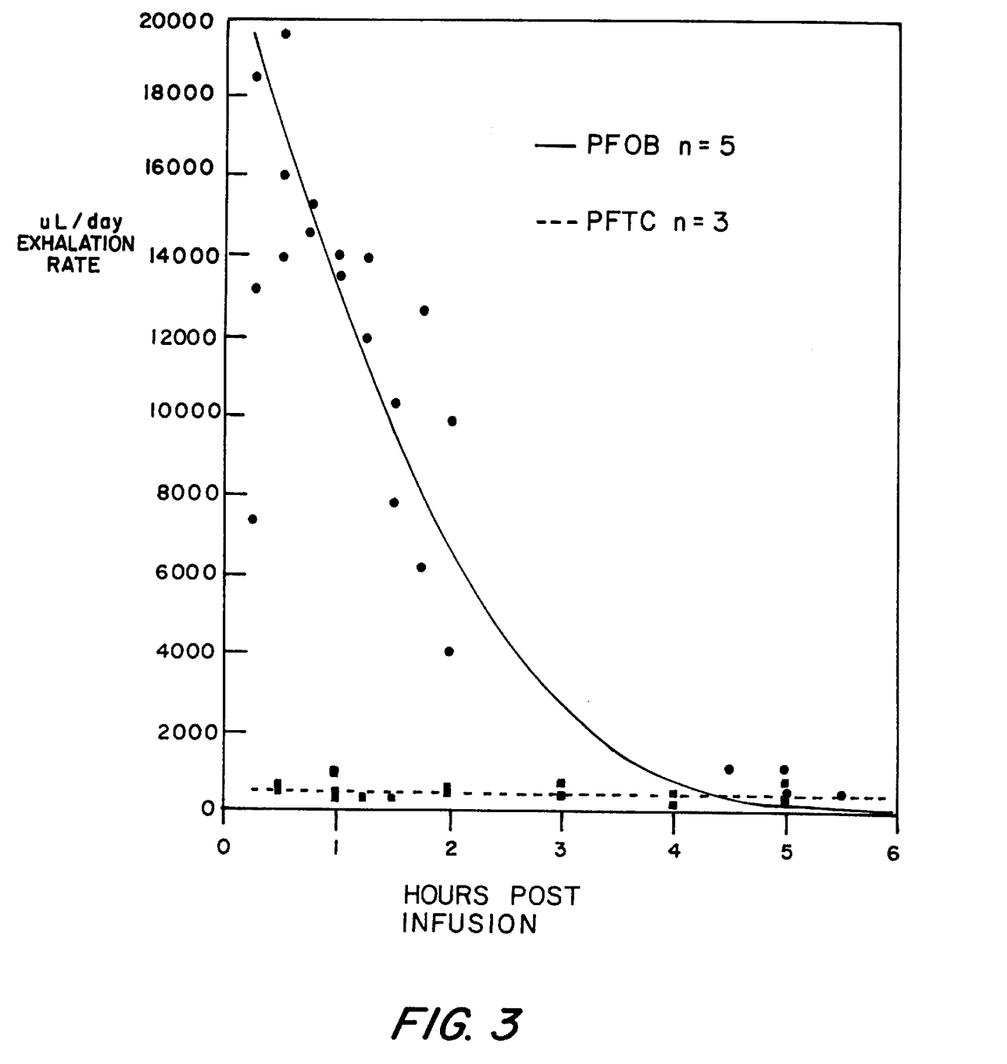
FIG. 3 shows a plot of the exhalation rate of perfluorotetramethylcyclohexane and perfluorooctylbromide as a percentage of the exhalation rate of perfluorooctylbromide over a six hour period.

FIG. 3 shows exhalation results over a period of six hours. This plot shows rates of PFC loss plotted as a percent of the initial rate of PFOB loss. The PFOB plot begins at 100%, but drops to nearly 0% at after six hours indicating that almost all of the readily-accessible PFOB has evaporated by that time. The steep drop of the PFOB plot represents a rapid decrease in the quantity of PFOB due to its volatility. Although the initial rate of PFTC may be nearly one-third as great as that of PFOB (initial rate of exhalation prior to first shown time point), it quickly drops to a steady lower rate which is less than 20% of the rate of PFOB exhalation. This slower but constant rate of PFTC exhalation indicates that accessible quantities of PFTC remain for at least six hours following administration.

While PFTC is likely to have an acceptably brief residence time, its residence in the lung is longer than PFOB, resulting in a longer therapeutic benefit from a given dose. The longer benefit encompasses several important advantages: costs are lowered because less material is used and less labor expended in administering the material; patient quality of life is enhanced because their is less invasive therapy; and overall environmental quality is improved because there is a smaller amount of PFC released to the environment.

When exploring the exhalation of PFCs from lungs over prolonged periods, completely unexpected results were encountered, particularly when the exhalation rates of perfluorocarbon mixtures were measured. There have been attempts to control the boiling points of therapeutic PFCs by mixing different PFCs together. It is generally believed that mixtures will show boiling points that are intermediate to those of the compounds that make up the mixture. However, HLS has been shown to be a vapor-based phenomena. That is, even if the apparent boiling point of a lung damaging PFC is raised by an admixture of a higher boiling point PFC, the characteristic HLS damage may still be caused by the vapors. This is particularly true because the quantity of various PFC vapors present are expected to be related to the vapor pressures of the individual PFCs rather than to the boiling point of the mixture.

Figure 4:
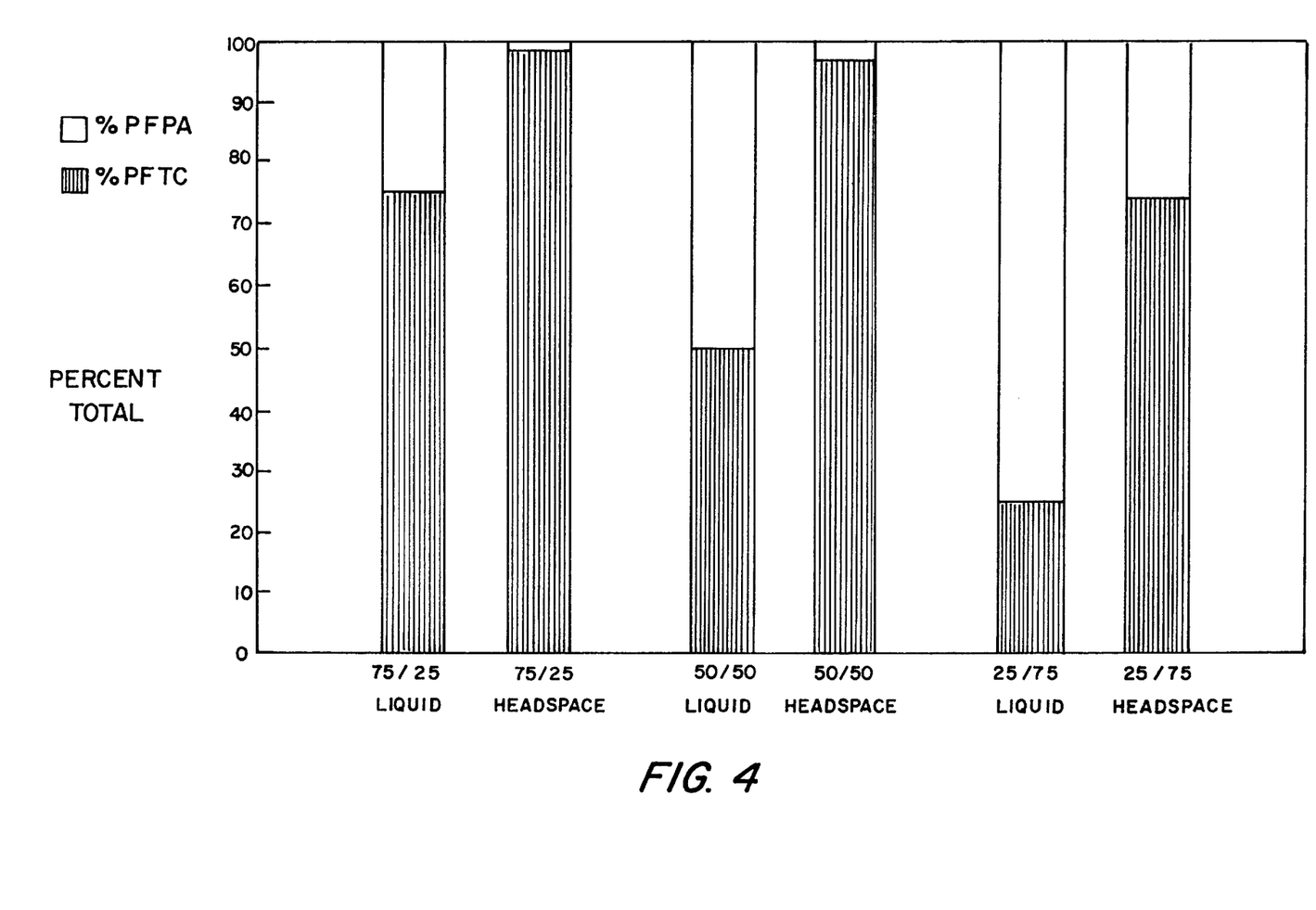
FIG. 4 shows the relationship between liquid mixtures of perfluorocarbon liquids and the quantity of the different perfluorocarbon vapors in the headspaces above the liquid mixtures.

Physical laws of gas behavior predict that the proportion of PFC species in the vapor phase above a mixture will be strongly influenced by the vapor pressure of the constituents of the mixture. It makes sense that molecules of compounds with a higher vapor pressure will preferentially leave the liquid mixture and enter the vapor phase above the mixture. This is illustrated in FIG. 4, which shows the actual quantity of PFC vapor above various mixtures. The first bar on the left represents a liquid mixture of 75 parts of PFTC and 25 parts PFPA per volume. The second bar shows the proportion of the PFC vapors measured in the headspace above this mixture. The vast majority of vapor is from the higher vapor pressure PFTC. If PFTC were an HLS causing compound, the lung tissue would experience vapor that was essentially all HLS causing.

The situation is only slightly changed in the next pair of bars, which represents a 50:50 mixture and the vapors measured above this mixture. Here the vapors are over 90% the higher vapor pressure compound. Again, the dominant vapor effect will be due to the higher vapor pressure material. Even in the third pair of bars, representing a 25:75 PFTC:PFPA mixture, the vapor phase is about 75% PFTC. It is clear that the use of mixtures is not a viable way of controlling vapor-induced lung damage caused by installation of very high vapor pressure fluorocarbons.

Figure 5:
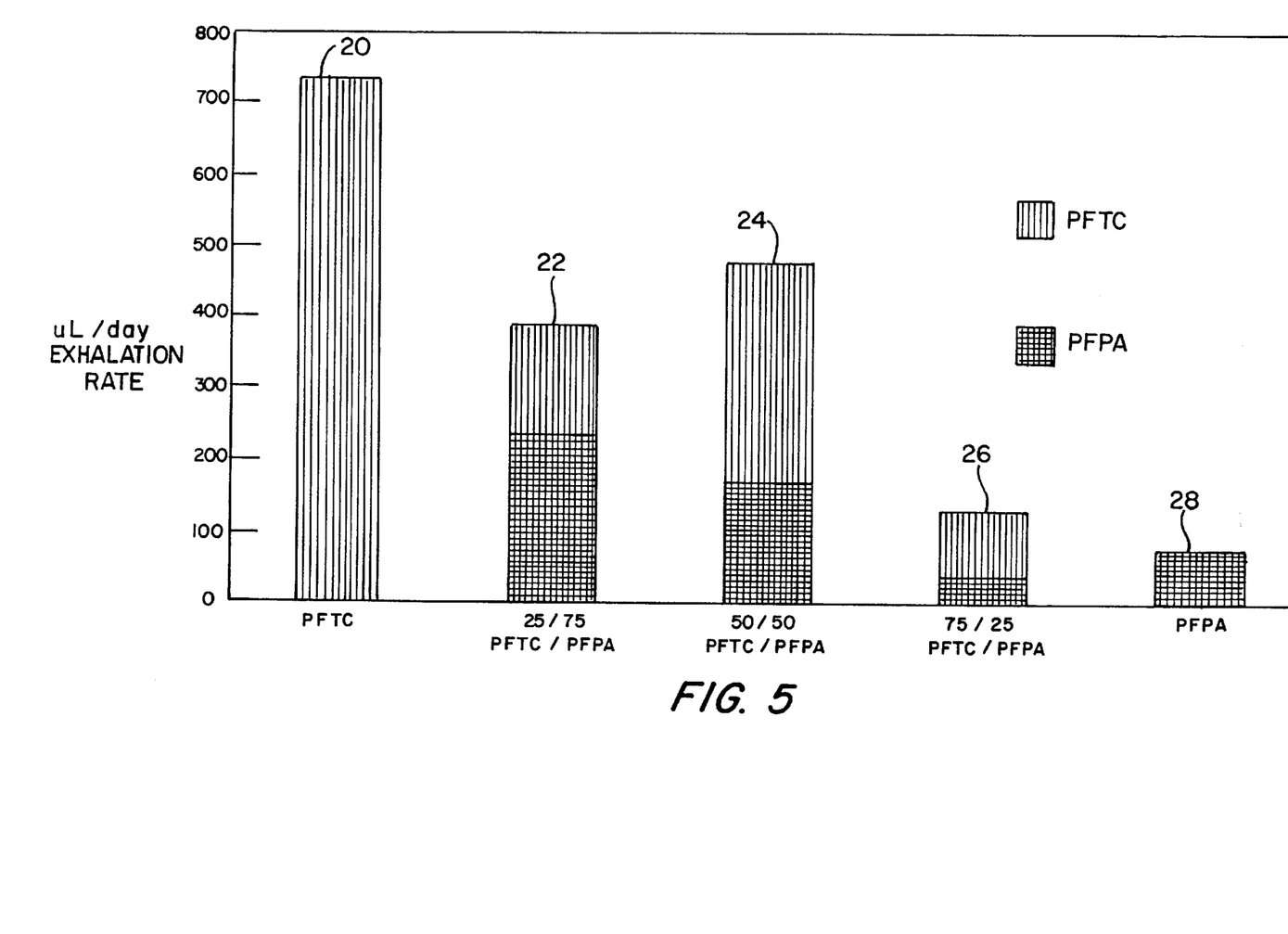
FIG. 5 shows the rates of exhalation of liquid perfluorocarbons and liquid perfluorocarbon mixtures from lungs of experimental animals one hour post instillation of the perfluorocarbons.

With these results as background, the present inventor was absolutely astounded by the results of actual measurements of PFCs exhaled from the lungs of experimental animals. Neat liquid PFCs were instilled into the lungs of matched young rats (body weight about 250 g) at a dosage of 6 ml/kg of body weight. FIG. 5 shows an analysis of exhaled PFC vapors one hour after the instillation of the PFCs. A left-hand bar 20 represents the exhalation rate of slightly over 700 $\mu$l/day PFTC in an animal that received 100% PFC. A right-hand bar 28 represents the exhalation rate of less than 100 $\mu$l/day for 100% PFPA. This is consistent with the much lower vapor pressure of PFPA.

A fourth bar 26 represent the exhalations from an animal receiving a 75:25 PFTC:PFPA mixture. Here the rate of PFPA exhalation is about half that of bar 28. From the headspace analysis in FIG. 4 one would anticipate that virtually no PFPA would be exhaled. The discrepancy is even more marked in a middle bar 24 which represents exhalation from an animal receiving a 50:50 mixture. The overall exhalation rate is reduced compared to 100% PFTC (bar 20), but the exhalation rate for PFPA is considerably greater than the rate shown in bar 28. Bar 22, representing the exhalation from a 25:75 PFTC:PFPA mixture, shows a rate of PFPA exhalation more than twice that of pure PFPA. These results suggest that the lower boiling PFTC is somehow potentiating the exhalation of higher boiling PFPA.

Figure 6:
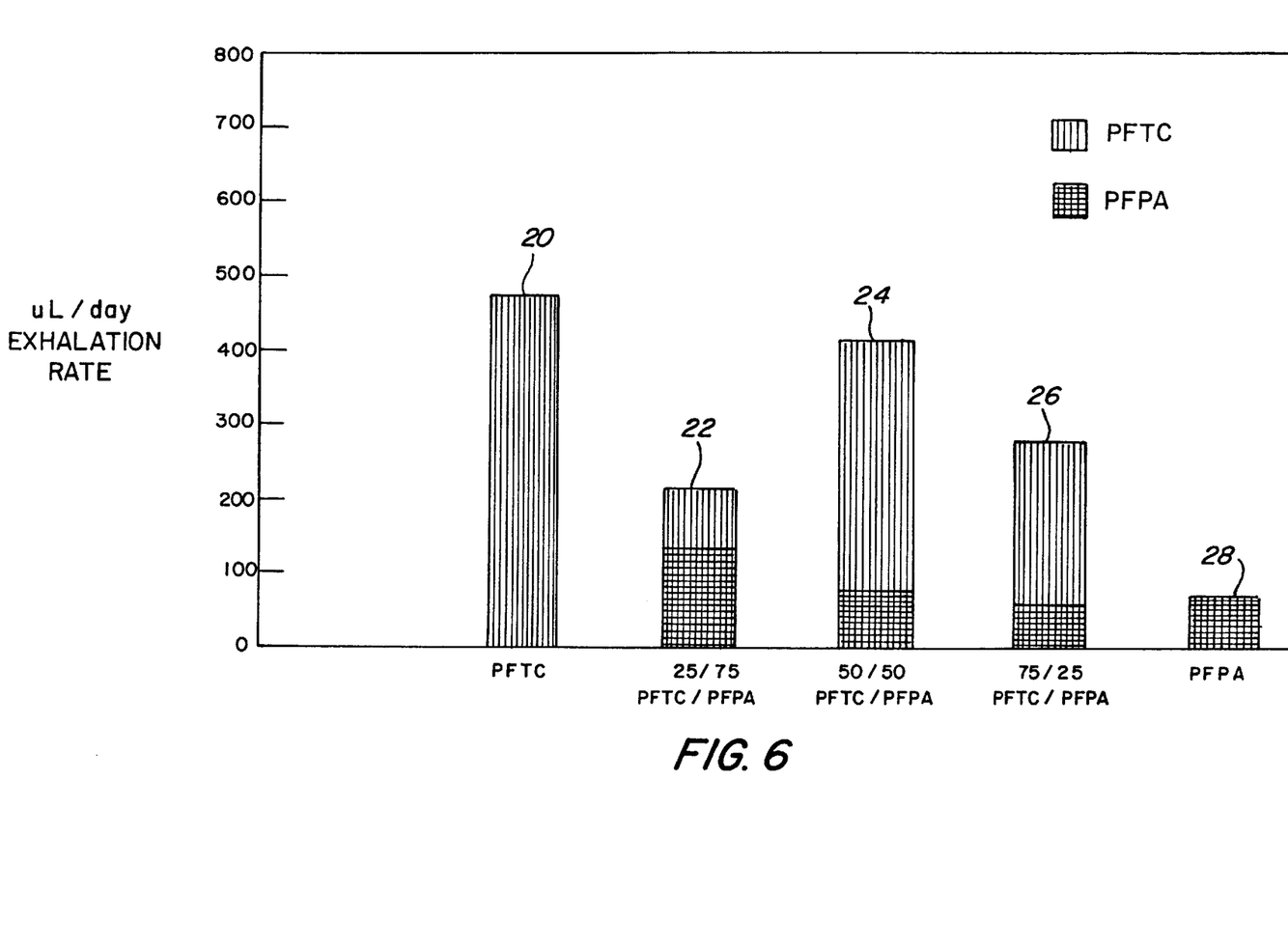
FIG. 6 shows the rates of exhalation of liquid perfluorocarbons and liquid perfluorocarbon mixtures from lungs of experimental animals 4.5 hours post instillation.

FIG. 6 shows an analysis of PFC vapor exhaled 4.5 hours after instillation. A left-hand 20 bar shows that an animal receiving pure PFTC exhaled about 475 $\mu$l/day of PFC. A right-hand bar 28 shows that an animal receiving a dose of pure PFPA exhaled only about 75 $\mu$l/day of PFC. Bar 26, which again represents exhalation from an animal dosed with a 75:25 mixture of PFTC:PFPA, shows a higher than expected rate of PFPA exhalation.

A similar pattern is seen with a second bar 22 and a third bar 24, which represent exhalation of 25:75 and 50:50 PFTC:PFPA mixtures, respectively. Both the 25:75 and the 50:50 mixtures actually show rates of exhalation of PFPA above that of pure PFPA, with the highest rate of PFPA exhalation being shown with the 25:75 mixture. However, the maximum exhalation rate for PFPA is somewhat less than that shown in FIG. 5. It appears that as the overall level of PFTC decreases due to exhalation, the rate of PFPA exhalation decreases. Note that the exhalation rate of pure PFPA (bar 28) is virtually unchanged suggesting that the amount of pure PFPA is not significantly reduced over this time period.

Figure 7:
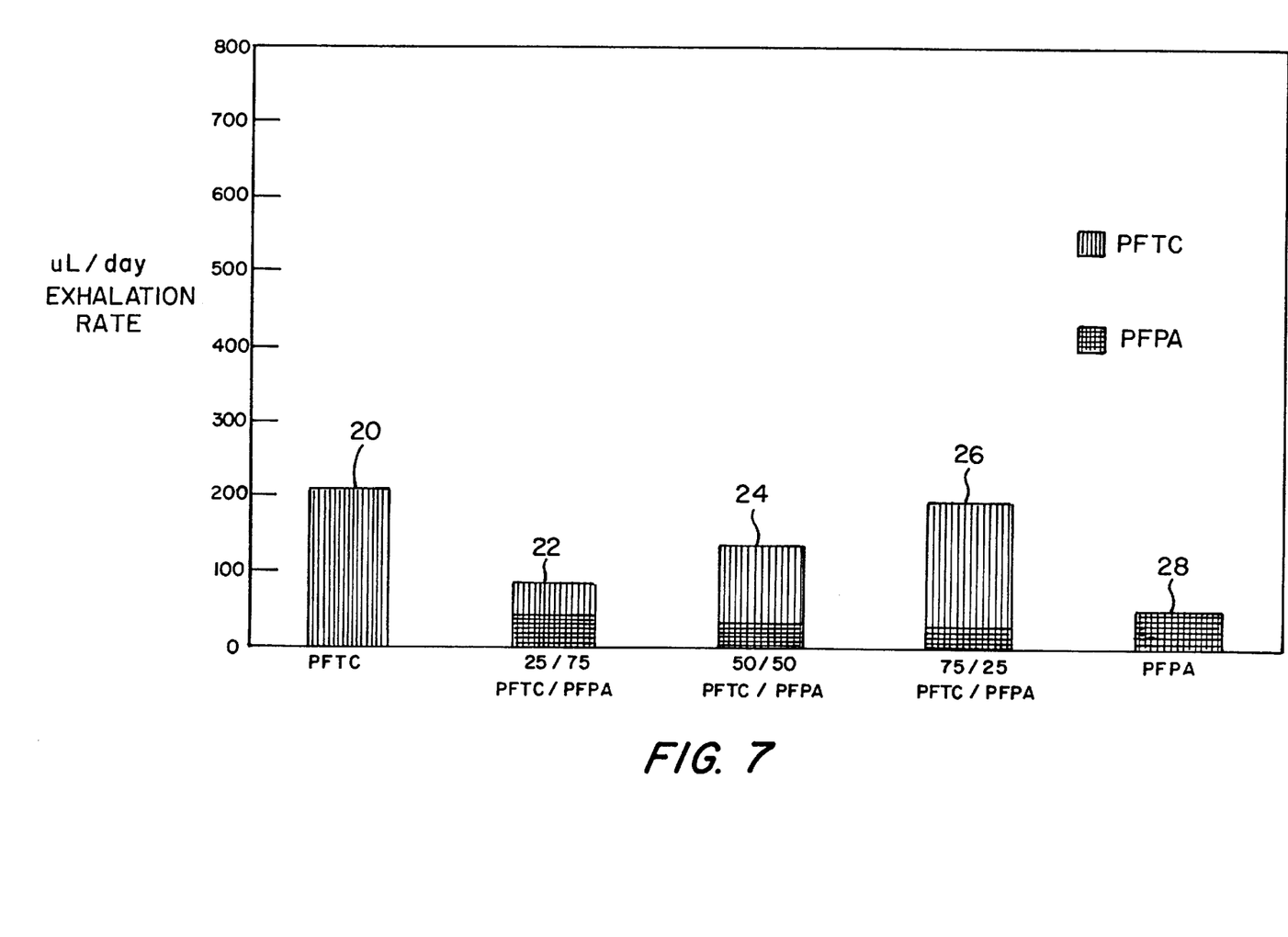
FIG. 7 shows the rates of exhalation of liquid perfluorocarbons and liquid perfluorocarbon mixtures from lungs of experimental animals one day post instillation.

FIG. 7 shows the exhalation rates one day post PFC instillation. Bar 28 shows that the rate of exhalation of pure PFPA is only slightly decreased as compared to FIG. 5. However, the rate of pure PFTC exhalation as represented by a left hand bar 20 is about one third the one hour rate, probably because the available quantity of PFTC has been decreased due to exhalation. The exhalation rates of mixtures (25:75, bar 22; 50:50, bar 26; and 75:25, bar 26) all show PFPA exhalation rates lower than that for pure PFPA.

The results of PFC mixture exhalation indicate that the vapor pressure-based theory of exhalation is somehow incorrect. It appears that the presence of a lower boiling point PFC such as PFTC actually potentiates the exhalation of a higher boiling point PFC such as PFPA. It also appears that the rate of exhalation is influenced by the proportions of the PFCs in the mixture. That is, in FIGS. 5 and 6, as the proportion of PFPA increases in a mixture, the amount of PFPA exhaled increases. The overall rate of exhalation also appears controlled by the characteristics of the mixture. In FIG. 6 the overall exhalation rate of the 50:50 mixture is nearly as great as pure PFTC. Surprisingly, the 75:25 PFTC:PFPA mixture shows a decreased overall rate of PFC exhalation.

It should be kept in mind that the ratios of PFCs in the lungs at 1 or 4.5 hours post instillation of PFC are almost certainly not the same as the ratios at instillation. Certainly, the vapor pressure model predicts that the initial loss of PFC from the lungs might be predominantly PFTC. Therefore, it might be expected that as time from instillation increases, the lungs would contain a higher level of PFPA relative to PFTC than in the initial mixtures. This does not, however, explain why the rate of PFPA exhalation is greater in the presence of PFTC. Some hitherto unrecognized process causes the presence of the lower boiling point PFC to accelerate the exhalation of the higher boiling point PFC.

The present inventor has not yet been able to entirely explain this completely unexpected phenomenon. Considering that many of the air passages of the mammalian lung are lined with ciliated cells, it is possible that the beating cilia move the PFC film about and actually shoot tiny droplets of the liquid into the moving air stream of the lungs. Suspended in air, the tiny droplets would completely vaporize and be exhaled. In this case the exhaled vapor might more closely reflect the proportion of PFCs in the mixture, rather than the vapor pressures of the constituent PFCs as had been expected. This still does not explain the apparent potentiating effect of PFTC on PFPA exhalation, but this potentiation may involve viscosity or other properties not yet considered. That is, the PFTC might mobilize the PFPA so that it can be more readily acted upon by cilia or whatever force is causing the anomalous exhalation.

Regardless of the cause of this phenomenon, these results completely alter the logic of PFC-assisted liquid breathing. Up to now many workers have experimented with relatively low boiling point PFCs, partly because of the fear that high boiling point PFCs would have dangerously long residence times in the lung. The drawback to this approach is that higher vapor pressure (low boiling point) PFCs vaporize too rapidly, requiring constant replenishment as well as specialized equipment to manage this replenishment. What is even worse, some of the most prevalent lower boiling point PFCs, like PFOB, are capable of causing HLS damage.

The above results have demonstrated that PFTC represents an ideal PFC in that it has a sufficiently low vapor pressure to completely avoid any HLS damage. A benefit of this lower vapor pressure is that PFTC may have a long enough residence time in the lungs to last through an entire treatment. For example, if PFTC is used to aid respiration in surfactant deficient lungs, the lungs may recover sufficiently to produce adequate surfactant before so much of the PFTC has been exhaled that an effective dose is no longer present. At any rate, the frequency of dosing with PFTC is significantly lower that required with PFOB.

However, there remain a number of lung disease states where the recovery period is so long that even the less frequent doses required with PFTC may become excessive. The ideal solution for these cases would be the use of a very low vapor pressure PFC such as PFPA as the primary therapeutic. However, until now this approach has not been favored because of the extremely long residence times of PFPA and other low vapor pressure PFC liquids. In the past, it has been contemplated that PFPA could be washed out of the lungs using a lavage of a higher vapor pressure PFC. However, before very recent availability of PFTC there was no completely safe PFC for such lavage. In any case, repeated lung lavage is difficult and traumatic. While possible with a laboratory animal, it would probably never be an acceptable medical procedure for human use.

Figure 8:
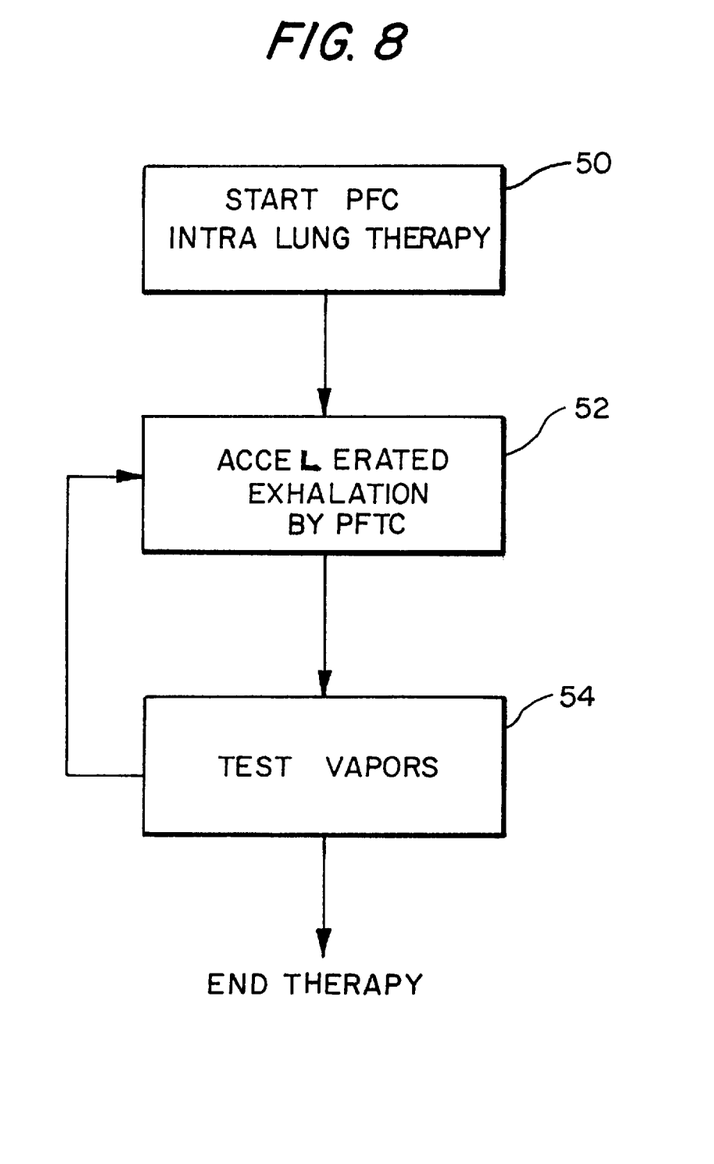
FIG. 8 shows a method of the current invention used to accelerate the exhalation of low vapor pressure perfluorocarbons from a patient's lungs following perfluorocarbon liquid breathing therapy.

However, now that it has been discovered that addition of PFTC greatly accelerates the exhalation of higher boiling point PFCs with no need to require traumatic lavage procedures to draw the PFC mixture from the lungs. Instead, a series of relatively small doses of PFTC administered over a period of days or weeks can be used to remove persistent PFCs from the lungs through accelerated exhalation. FIG. 8 illustrates the method made possible by this new discovery. In a first step 50 PFC breathing therapy is initiated. The therapy involves instilling an effective quantity of a safe PFC into the lungs of a patient. If the therapy is expected to be of very short duration (i.e., a day), PFTC alone might be used. More usually, long-term therapy is envisioned. In that case a more persistent (higher boiling point) PFC is instilled into the lungs. Depending on the required length of treatment, a safe PFC such as PFMD could be used. For a very lengthy treatments PFPA is probably the PFC of choice.

Mixtures of these PFCs can also be employed. A mixture of higher boiling point PFC(s) and PFTC could be used to help distribute the higher boiling point PFC(s) and to speed its (their) initial exhalation. That is, initiation of liquid breathing therapy could be made using a mixture of PFTC and a higher boiling point (lower vapor pressure) PFC so that there is a longer, but not excessively long, residence of an effective quantity of PFC.

The first step 50 might also include repeated dosing with safe PFC to maintain a desired therapeutic level of PFC. However, at some point it would be concluded that therapy should end. This is accomplished by a second step 52 in which one or more doses of a safe lower boiling point PFC such as PFTC is instilled into the lungs. This material accelerates the exhalation of any higher boiling point PFCs previously used. Depending on the initial mixture and dosage employed, it might be necessary to follow the initial dose with one or more doses of PFTC to complete the removal of the higher boiling point (lower vapor pressure) PFC in a timely fashion. The exhaled breath can be periodically tested, in a third step 54, for presence of the lower vapor pressure PFC(s). Depending on the level of lower vapor pressure PFC detected, the second step 52 is repeated to continue the removal of the lower pressure PFC. When the exhaled level of these persistent PFCs approaches zero, the therapy is concluded and the patient discharged.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method of facilitating transport of gases in a biological system, the improvement comprising using as the gas transport agent a perfluorinated compound having the following structure wherein ring carbons are fully fluorinated:

2. The method of claim 1 wherein the compound has the following structure:

3. The method of claim 1 wherein the compound has the following structure:

4. The method of claim 1 wherein the compound has the following structure:

5. A method of facilitating transport of oxygen in liquid breathing therapy of a mammal, the method comprising the step of instilling, as a gas transport agent, into the lungs of the mammal a perfluorinated compound of the formula wherein ring carbons are fully fluorinated:

6. The method of claim 5, wherein the compound has the following structure:

7. The method of claim 5 wherein the compound has the following structure:

8. The method of claim 5 wherein the compound has the following structure:

9. The method of claim 5, wherein the perfluorinated compound is in an aqueous emulsion.

10. A method of liquid breathing therapy for a mammal comprising the steps of:
   instilling into lungs of the mammal an effective amount of a first perfluorocarbon liquid sufficient to promote gas exchange and lung expansion, the first perfluorocarbon liquid having a sufficiently high boiling point that a quantity of the perfluorocarbon liquid remaining in the lungs after one day is sufficient to maintain gas exchange and lung expansion; and
   accelerating the exhalation of the first perfluorocarbon liquid by instilling into the lungs a second perfluorocarbon liquid, the second perfluorocarbon liquid having a boiling point lower than the first perfluorocarbon liquid but sufficiently high to avoid hyperinflation of the lungs.

11. The method of claim 10, wherein the step of instilling the first perfluorocarbon liquid is replaced by a step of instilling a mixture of the first and the second perfluorocarbon liquids.

12. The method of claim 10, wherein the second perfluorocarbon liquid is instilled as a plurality of separate sequential doses.

13. The method of claim 10, wherein the ratio between the first and the second perfluorocarbon liquids in the accelerating step is adjusted to maximize the exhalation rate of the first perfluorocarbon liquid.

14. The method of claim 10, wherein the second perfluorocarbon liquid is perfluorotetramethylcyclohexane.

15. The method of claim 14, wherein the perfluorotetramethylcyclohexane is instilled as a plurality of separate sequential doses.

16. The method of claim 10 wherein the first perfluorocarbon liquid is perfluorophenanthrene and the second perfluorocarbon liquid is perfluorotetramethylcyclohexane.

17. The method of claim 16, wherein the perfluorotetramethylcyclohexane is instilled as a plurality of separate sequential doses.

18. The method of claim 16, wherein the ratio between the perfluorophenanthrene and the perfluorotetramethylcyclohexane in the accelerating step is adjusted to maximize the exhalation of the perfluorophenanthrene.

19. A method of accelerating the exhalation of a first perfluorocarbon liquid having a boiling point above about 160° C. from lungs of a mammal, the first perfluorocarbon liquid having been previously instilled into the lungs of the mammal as a gas transport agent, the method comprising:
   a first step of instilling an effective amount of a second, lower boiling point perfluorocarbon liquid into the lungs, the second lower boiling point perfluorocarbon liquid causing an accelerated rate of exhalation of the first higher boiling point perfluorocarbon liquid;
   a second step of analyzing exhaled perfluorocarbon vapors to determine exhalation rates of both perfluorocarbon liquids; and
   a third step of repeating the first and the second steps until the exhalation rate of the first higher boiling point perfluorocarbon liquid is acceptably low.

20. The method of claim 19, wherein the lower boiling point perfluorocarbon liquid has a boiling point higher than about 141° C.

21. The method of claim 19, wherein the lower boiling point perfluorocarbon liquid is perfluorotetramethylcyclohexane.

22. A method of accelerating the exhalation of a perfluorocarbon liquid having a boiling point above about 160° C. from lungs of a mammal comprising instilling an effective amount of perfluorotetramethylcyclohexane into the lungs, the perfluorotetramethylcyclohexane causing an accelerated rate of exhalation of the higher boiling point perfluorocarbon liquid.

* * * * *